United States Patent [19]
Casey et al.

[11] Patent Number: 5,571,687
[45] Date of Patent: Nov. 5, 1996

[54] MODULATORS OF MULTIDRUG RESISTANCE TRANSPORTERS

[75] Inventors: Patrick J. Casey; Lili Zhang, both of Durham, N.C.

[73] Assignee: Duke University, Durham, N.C.

[21] Appl. No.: 257,321

[22] Filed: Jun. 7, 1994

[51] Int. Cl.$^6$ ............................. C12Q 1/00; C12Q 1/02; G01N 33/48
[52] U.S. Cl. .................... 435/29; 435/4; 435/34; 435/69.1; 435/69.7; 435/7.21; 435/7.1; 435/15; 436/63; 514/1; 514/22; 514/23
[58] Field of Search .................... 435/29, 4, 34, 435/7.21, 7.23, 69.1, 69.7, 15, 7.1; 514/350, 449, 343, 357, 1, 22, 23, 437; 436/548, 63

[56] References Cited

U.S. PATENT DOCUMENTS

| | | | |
|---|---|---|---|
| 4,990,538 | 2/1991 | Harris et al. | 435/29 |
| 5,043,268 | 8/1991 | Stock | 435/15 |
| 5,104,858 | 4/1992 | Hait et al. | 514/437 |
| 5,166,059 | 11/1994 | Pastan et al. | 435/69.7 |
| 5,366,885 | 11/1994 | Barranco, III | 435/7.23 |
| 5,369,009 | 11/1994 | Arceci et al. | 435/7.23 |

OTHER PUBLICATIONS

Philips et al, "Carboxyl Methylation of Ras–Related Proteins During Signal Transduction in Neutrophils", Science 259:977–980 (1993).

Michaelis, "STE6, the yeast a–factor transporter", Cell Biology 4:17–27 (1993).

Raymond et al, "Functional Complementation of Yeast ste6 by a Mammalian Multidrug Resistance mdr Gene", Science 256:232–234 (1992).

Nakagawa et al, "Reversal of Multidrug Resistance by Synthetic Isoprenoids in the KB Human Cancer Cell Line", Cancer Research 46:4453–4457 (1986).

Yamaguchi et al, "Overcoming Drug Resistance in Cancer Cells With Synthetic Isoprenoids", JNCI 76(5):947–953 (1986).

Akiyama et al, "Synthetic Isoprenoid Photoaffinity Labeling of P–Glycoprotein Specific to Multidrug–Resistance Cells", Molecular Pharmacology 36:730–735 (1989).

Nakagawa et al, Cancer Res, vol. 46, pp. 4453–4457, Sep. 1986.

Raymond et al, Science, vol. 256, 232–234, 1992.

Primary Examiner—Douglas W. Robinson
Assistant Examiner—Louise N. Leary
Attorney, Agent, or Firm—Nixon & Vanderhye P.C.

[57] ABSTRACT

The present invention relates, in general, to multidrug resistance and, in particular, to compounds that modulate multidrug resistance transporters. The invention also relates to methods of selecting or designing compounds for the ability to modulate multidrug resistance transporters, and to methods of modulating multidrug resistance.

17 Claims, 6 Drawing Sheets

MODULATORS OF MULTIDRUG RESISTANCE TRANSPORTERS

FIELD OF THE INVENTION

The present invention relates, in general, to multidrug resistance and, in particular, to compounds that modulate multidrug resistance transporters. The invention also relates to methods of selecting or designing compounds for the ability to modulate multidrug resistance transporters, and to methods of modulating multidrug resistance.

BACKGROUND

Overexpression of the integral membrane protein P-glycoprotein (P-gp, also known as the multidrug resistance (MDR) transporter) is the most common characteristic associated with tumor cells that have developed drug resistance to antineoplastic agents (Gottesman et al, Ann. Rev. Biochem. 62:385 (1993), Endicott et al, Ann. Rev. Biochem. 58:137 (1989)). In this type of drug resistant cell, P-gp functions as an energy-dependent drug efflux pump that can transport a broad spectrum of structurally unrelated cytotoxic and anticancer drugs.

P-glycoprotein is the product of the MDR1 gene. Homologous mammalian genes include the highly-related MDR2 gene and the MRP (for multidrug transporter related protein) gene (Gottesman et al, Ann. Rev. Biochem. 62:385 (1993); Cole et al, Science 258:1650 (1992)). To date, only the product of the MDR1 gene (ie P-glycoprotein) has been shown to be significantly associated with multidrug resistance. Additionally, the product of a related gene, pfmdr, in *Plasmodium falciparum* (the organism that causes malaria) has been implicated in chloroquine resistance in this parasite (Cowman et al, Seminars Cell Biol. 4:29 (1993)). Drug resistance in other parasites, eg trypanosomes, may also involve membrane transporters of the general structure of P-gp (Carter et al, Nature 361:173 (1993)).

P-glycoprotein belongs to a superfamily of membrane-associated transporters termed the ATP-binding cassette (ABC) family or the Traffic ATPase family (Higgins, Ann. Rev. Cell Biol. 8:67 (1992)). In mammalian cells, the best-known members of this family, in addition to P-gp, are the CFTR protein, the product of the cystic fibrosis gene (Welsh et al, Neuron 8:821 (1992)), a peroxisomal membrane protein termed PMP70 which has been implicated in the biogenesis of this organelle (Gartner et al, Seminars Cell Biol. 4:45 (1993)), and members of the family of adenylyl cyclases, the enzymes responsible for the production of cAMP as a second messenger (Tang et al, Cell 70:869 (1992)).

One such transporter similar to P-gp, termed Ste6, has been found in *Saccharomyces cerevisiae* to be responsible for the export of the peptide mating pheromone, a-factor (Michaelis, Seminars in Cell Biol. 4:17 (1993)). In a Ste6 deletion mutant, expression of a mammalian P-gp gene has been shown to complement the function of Ste6 and restore low, but detectable, mating activity (Raymond et al, Science 256:232 (1992)). Homology between P-gp and Ste6 thus appears to exist, from the standpoint of both function and structure.

Mature a-factor is a dodecapeptide containing a post-translationally modified C-terminus (Anderegg et al, J. Biol. Chem. 263:18236 (1988)). More specifically, the C-terminus of a-factor is subject to post-translational modification via the process of prenylation (Clarke, Ann. Rev. Biochem. 61:355 (1992)). Proteins subjected to this processing contain a cysteine residue at or near their C-terminus and are modified by attachment of either a 15-carbon farnesyl or a 20-carbon geranylgeranyl isoprenoid to the cysteine residue. The majority of prenylated proteins, which include Ras and most G proteins (Casey, Curr. Opinion Cell. Biol. 6:219 (1994)), are further modified by methylation on the carboxyl group of the prenylated cysteine.

Prenylation has been found to be a stable modification (Casey et al, Proc. Natl. Acad. Sci. USA 86:8323 (1989)) and prenylated proteins have been reported to comprise up to 2% of total cellular protein (Epstein et al, Proc. Natl. Acad. Sci. USA 88:9668 (1991)). These factors raise the question of how cells dispose of isoprenoid-modified cysteines produced during protein turnover. Effective disposal may be important as accumulation of such metabolites in cells could result in critical problems due to the fact that certain prenylcysteines can inhibit cellular processes such as protein methylation and signal transduction (Hazoor-Akbar et al, Proc. Natl. Acad. Sci. USA 90:868 (1993), Philips et al, Science 259:977 (1993)).

Prenylcysteine methyl esters, corresponding to the C-terminus of prenylated proteins, have now been identified as substrates for P-gp. This finding has provided an answer to the question of how the cell rids itself of potentially toxic metabolites and has provided basis for the present invention.

SUMMARY OF THE INVENTION

In one embodiment, the present invention relates to a method of inhibiting or reversing the resistance of cells to the effects of a drug. The method comprises contacting the cells with a compound, or pharmaceutically acceptable salt thereof, of the formula:

wherein:

$R^1$ is a hydrophobic moiety;

$R^2$ is an uncharged moiety; and $NR^3$ is a cationic moiety or uncharged moiety, in an amount sufficient to effect the inhibition or reversal.

In another embodiment, the present invention relates to a method of assaying a test compound for the ability to competitively inhibit a P-glycoprotein (P-gp)-associated activity. The method comprises reacting the test compound with P-glycoprotein in the presence of a compound of formula:

wherein:

$R^1$ is a hydrophobic moiety;

$R^2$ is an uncharged moiety; and $NR^3$ is a cationic moiety or uncharged moiety, and comparing the resulting P-gp-associated activity with that of a control sample, an inhibition in P-gp-associated activity being indicative of a competitive inhibitor.

In a further embodiment, the present invention relates to a method of blocking a membrane transporter of a cell. The method comprises contacting the cell with a compound, or pharmaceutically acceptable salt thereof, of the formula wherein:

$R^1$ is a hydrophobic moiety;

$R^2$ is an uncharged moiety; and $NR^3$ is a cationic moiety or uncharaged moiety, in an amount sufficient to effect the blocking.

In yet another embodiment, the present invention relates to N-acyl-S-prenylcysteine C-alkylamide or S-prenylcysteine C-alkylamide.

Objects and advantages of the invention will be clear from the description that follows.

BRIEF DESCRIPTION OF THE DRAWINGS

FIG. 1. P-gp expression in Sf9 cells and in human breast cancer MCF7 cells.

A. Immunblot detection. Membranes (10 μg protein) prepared from MDR1-baculovirus infected Sf9 cells (lane 1), mock-infected Sf9 cells (lane 2), drug-resistant MCF7-MDR cells (lane 3) and drug-sensitive MCF7-WT cells (lane 4) were processed by 9% SDS-PAGE and proteins were transferred to nitrocellulose membranes. Expression of P-gp was detected with monoclonal antibody C219 and alkaline phosphatase conjugated anti-mouse secondary antibody.

B. Drug-dependent ATPase activity. Membranes (5–10 μg protein) were incubated in the presence of vehicle (–) or in the presence of 10 μM verapamil (VRP) (+) as described in the text. P-gp-associated ATPase activity was measured as inorganic phosphate release from ATP.

FIG. 2. Effect of prenylcysteine compounds on the ATPase activity of P-gp.

A. Human MDR1 expressed in Sf9 cells.

B. MCF7-FDR cell membranes.

ATPase assays were conducted as described above in connection with FIG. 1. Compounds were dissolved in DMSO and final DMSO concentration in the ATPase reaction was maintained at 1%. Symbols used are: FCME, (●); FC, (○); GGCME, (▲); GGC, (△); VRP, (X) . The data shown are from one experiment with each of the two cell types and are representative of five independent membrane preparations from Sf9 cells and three membrane preparations for MCF7-MDR cells.

FIG. 4. Interaction of prenylcysteine methylamides and prenylcysteine-containing dipeptides with P-gp. The compounds were purified by reversephase HPLC chromatography and analyzed for their ability to stimulate the ATPase activity of P-gp in Sf9 membranes and, in the case of AFCMA, to inhibit FCME-stimulated ATPase activity as described for AFCME in Example 4. Left panel—Stimulation of P-gp ATPase activity in Sf9 membranes. Increasing concentration of FCMA (■), farnesylated γGlu-Cys (unmethylated F-dipeptide, △), and the methylated form of farnesylated γGlu-Cys (methylated F-dipeptide, ▲) were analyzed. Right panel AFCMA inhibition of P-gp ATPase activity in Sf9 membranes. Increasing concentrations of AFCMA were added to membranes from Sf9 cells expressing P-gp either with no added drug (○) or along with 20 μM AFCME as an ATPase stimulator (●).

FIG. 5. Effect of prenylcysteine compounds on [$^3$H]-azidopine labelling of P-gp expressed in Sf9 cells. Membranes from mock-infected Sf9 cells (lane 1) and MDR1-infected Sf9 cells (lanes 2–11) were photolabelled with [$^3$H]-azidopine in the absence of competing drug (lanes 1 and 2) or in the presence of nicardipine (NCP, lanes 3–5), FC (lanes 6–8) and FCME (lanes 9–11). Membranes (containing 50–60 μg protein) were incubated in the presence of either the indicated compounds or DMSO (0 drug) for 30 minutes at 20° C. in 10 mM Tris-HCl pH 7.5, 0.25 M sucrose. [$^3$H]-azidopine (52 Ci/mmol) was added to a final concentration of 0.5 μM and the samples were incubated an additional 20 min, followed by photolabelling on ice by UV irradiation for 10 min. Samples were processed on 7.5% SDS-polyacrylamide gels and photolabeled bands detected by fluorography.

DETAILED DESCRIPTION OF THE INVENTION

The present invention is based, at least, in part, on the identification of prenylcysteine compounds as substrates for the MDR transporter, P-gp. That identification makes possible the design and/or selection of pharmaceutically acceptable agents that can be used to modulate drug transport mediated by P-gp or transporter structurally related thereto. Such agents can be used to eleviate a major problem in chemotherapy (eg, cancer chemotherapy) — drug resistance. By inhibiting the ability of the target cell transporter to eliminate drug, the toxicity of the drug to the target cell, and thus the chemotherapeutic effectiveness of the drug, can be maintained.

physiologic and non-physiologic compounds, including prenylcysteines and analogs thereof, can be tested in vitro for their ability to serve as P-gp substrates (and thus modulators of MDR transporter activity), both in terms of stimulating the intrinsic ATPase activity of the transporter and competing for drug binding. Insect cells (eg Sf9 cells) infected with baculovirus containing MDR1 cDNA (available from the American Type Culture Collection, Rockville, Md.) can be used as a source of membranes suitable for use in such in vitro screens. Membranes from drug-induced resistant cells can also be used (eg, MCF7-MDR breast cancer cells). Details of an appropriate protocol for testing compounds for their ability to stimulate P-gp-associated ATPase are given in the Examples. The method described involves incubating MDR transporter-containing membranes with the test compound and measuring the level of vanadate sensitive release of inorganic phosphate from ATP (see Sarkadi et al, J. Biol. Chem. 267:4854 (1992)).

The ATPase assay can also be used to identify test compounds that inhibit P-gp activity, ie P-gp antagonists, which are also potential agents for reversing P-gp-mediated drug resistance. In this type of assay, the ability of a selected test compound to reduce P-gp-ATPase which has been stimulated by a drug known to elicit this activity (eg verapimil or farnesylcysteine methyl ester (FCME) is examined. Increasing concentrations of the selected test compound and a fixed amount of the stimulatory drug are mixed, added to the P-gp preparation, and ATPase activity determined. A dose-dependent inhibition of ATPase activity by the selected compound indicates an antagonist.

The ability of test compounds to compete for drug binding can be assessed using MDR transporter-containing membranes, as described above, and a known substrate of P-gp. A typical screening assay is referred to in Example 5. There, the ability of a test compound to compete for labelling of MDR by $^3$H-azidopine (a radiolabelled, photo-activatable MDR substrate) is assessed.

Compounds can also be tested for their suitability for use as modulators of the MDR transporter by assessing their ability to reverse resistance of drug resistant cells. An example is the use of MCF7-MDR breast cancer cells (which display resistance to adriamycin and other therapeutic agents) are used. The resistance of these cells is a result of expression of P-gp at high levels. Using this model, MDR-reversing and modulatory agents can be identified by studying the drug-survival characteristics of the parent (non-resistant) MCF-7 cells (MCF7-WT) in parallel as controls. In these experiments, the $EC_{50}$ for drug toxicity is determined for both MCF7-MDR and MCF7-WT cells in culture. The cells are plated in a medium containing increasing concentrations of cytoxic drug in the presence and absence of the test compound. Optimal concentrations of test compound and timing of addition are determined empirically. A decrease in the $EC_{50}$ for drug toxicity toward MCF7-MDR cells in the presence of the test compound is indicative of a decreased ability of the MDR transporter to eliminate drug from the cells and identifies the test compound as an inhibitor of MDR transporter activity.

Use of the screening protocols referenced above has resulted in the identification of compounds that can modulate the activity of P-gp. These compounds, which are within the scope of the invention, have the properties characteristic of MDR substrates or competitive inhibitors of the transporter. Certain of these compounds, though structurally distinct from known P-gp substrates, contain the characteristic cationic and hydrophobic moieties present in many such substrates. Specific compounds of the invention identified using the screens described herein are prenylcysteine methyl esters and methyl amides. These compounds interact with P-gp via their isoprenoid moiety, carboxyl or amide methyl group, and positive charge of the protonated amino group.

Preferred compounds of the invention include the methyl esters and methyl amides of farnesyl- and geranylgeranyl-cysteine and the N-acetylated versions of the compounds. Also included are the corresponding versions of short peptides which contain an S-prenyl group, eg farnesylated γ-glutamyl-cysteine methyl ester and its methyl amide, and any compound of the general structure which includes an S-prenyl cysteine and a cysteinyl-COOH group that has been derivatized such that the negative charge character of the group is reduced or eliminated. The invention includes not only the compounds identified above but also physiologically acceptable molecules designed so as to mimic these compounds. Such mimics include the placement of hydrophobic elements (eg acyl or phenyl chains) on the sulfhydryl group of a cysteine residue and the derivatization of the cysteinyl-COOH group so as to reduce or eliminate its charge. Included within the scope of these compounds are those that are modified at the cysteinyl-NH$_2$ group so as to increase activity toward, or antagonism of, the function of P-gp and related proteins (eg the products of the MDR2 and MRP genes, and the pfmdr gene product in *P. falciparum*).

Summarizing, the present invention relates to the use of compounds, and pharmaceutically acceptable salts thereof, of the formula:

wherein:
- $R^1$ is a hydrophobic moiety;
- $R^2$ is an uncharged moiety; and
- $NR^3$ is a cationic moiety or uncharted moiety.

In a preferred embodiment,
- $R^1$ is a hydrocarbon of 5–25 carbon atoms or an acyl of 5–25 carbon atoms;
- $R^2$ is —CH$_3$, —NH$_2$, —OX, —NHX, —NX$_2$, —CH$_2$X, —CH(X)$_2$ or —C(X)$_3$, wherein X is a hydrocarbon of 1–20 carbon atoms; and
- $NR^3$ is —NH$_3^{3O}$, —N(Y)$_3^+$ wherein Y is hydrogen or a hydrocarbon of 1–20 carbon atoms, —NHCOZ wherein Z is a hydrocarbon of 1–20 carbon atoms, or an amino acid residue.

In a more preferred embodiment,
- $R^1$ is a phenyl, a straight or branched chain alkyl, alkene or alkyne of 5–25 carbon atoms, or an acyl of 5–25 carbon atoms;
- $R^2$ is —CH$_3$, —NH$_2$, —OX, —NHX, —NX$_2$, —CH$_2$X, —(CH$_2$)$_n$CH(X)$_2$ or —(CH$_2$)$_n$C(X)$_3$, wherein n is 1–5 and X is a hydrocarbon of 1–4 carbon atoms; and
- $NR^3$ is —NH$_3^+$, —N(Y)$_3^+$ wherein Y is hydrogen or a hydrocarbon of 1–4 carbon atoms, —NHCOZ wherein Z is a hydrocarbon of 1–4 carbon, or an amino acid residue.

In a most preferred embodiment,
- $R^1$ is a straight or branched chain alkyl, alkene or alkyne of 10–20 carbon atoms;
- $R^2$ is —CH$_3$, —NH$_2$, —OX, —NHX, —NX$_2$, —CH$_2$X, —(CH$_2$)$_n$CH(X)$_2$ or —(CH$_2$)$_n$C(X)$_3$, wherein n is 1–5 and X is an alkyl of 1–4 carbon atoms;
- $NR^3$ is —NH$_3^+$, —N(Y)$_3^+$ wherein Y is hydrogen or an alkyl of 1–4 carbon atoms, —NHCOZ wherein Z is an alkyl of 1–4 carbon atoms, or an amino acid residue.

The prenylcysteine compounds identified above as P-gp substrates can be used in screening protocols, such as those described above, to assess the ability of a test compound to competitively inhibit P-gp-mediated transport. By way of example, a test compound can be added in increasing concentrations to a reaction mixture comprising a prenylcysteine methyl ester and a membrane source of MDR transporter and the effect on ATPase activity associated with the transporter determined. The kinetics of inhibition resulting from the test compound can be used to establish whether the test compound is a competitive inhibitor. Such inhibitors are within the scope of the invention. This type of screen is advantageous over similar protocols using currently available compounds as ATPase stimulators, since the prenylcysteines appear to represent physiological substrates and thus can lead to the identification of compounds that would be missed in current protocols.

The present invention further relates to pharmaceutical compositions comprising, as active agent, a compound described above and a pharmaceutically acceptable carrier. The appropriate concentration of active agent to be included in the composition can be readily determined by one skilled in the art. The concentration can be expected to vary depending, for example, on the compound and the dosage regimen used. The composition can be in a form suitable, for example, for injection (in which case, the composition is advantageously sterile), for oral administration (eg a tablet or capsule) or for topical administration (eg a cream, gel, lotion or ointment). The active agent can be administered in liposomes. The appropriate dosage regimen can be selected based on the compound used, the patient treated and the effect sought. Optimum regimens can be readily determined by one skilled in the art.

The invention also relates to methods of inhibiting transporter-mediated drug transport (eg MDR-mediated transport) and thereby maintaining effectiveness of a chemotherapeutic agent. The method involves contacting cells (procaryotic or eucaryotic cells, eg mammalian cells, human or non-human mammalian cells) that are the target of the chemotherapeutic agent with a compound of the invention under conditions such that transport (export) of the chemotherapeutic agent from the cell is inhibited. Typically, a sample of tissue under chemotherapy is examined for amplified expression of the membrane transporter (eg P-glycoprotein) through use of antibodies to the transporter, or DNA probes, to determine whether amplification of the transporter gene has occurred. Tissues displaying high levels of transporter expression are candidates for treatment with a combination of the chemotherapeutic agent and a compound of the invention (eg a P-gp antagonist such as a prenylcysteine). The compound of the invention can be administered several hours prior to administration of the chemotherapeutic agent, however, co-administration of the compounds may be effective under certain conditions. Co-formulations of a compound of the invention and the chemotherapeutic agent are thus within the scope of the invention.

Certain aspects of the invention are described in greater detail in the non-limiting Examples that follow.

EXAMPLES

The following experimental details and methodologies are referenced in the specific Examples set forth below.

Synthesis of Prenylcysteine Analogs

S-farnesylcysteine (FC), S-farnesylcysteine methyl ester (FCME) and N-acetyl-S-farnesylcysteine (AFC) were synthesized by alkylation of the sulfhydryl groups on cysteine, cysteine methyl ester (Sigma) or N-acetyl-cysteine (Sigma), respectively, with farnesyl bromide (Aldrich) as described (Brown et al, J. Am. Chem. Soc. 113:2176 (1991)). The same method was applied to the synthesis of S-geranylgeranylcysteine (GGC) and S-geranylgeranylcysteine methyl ester (GGCME) for which the sulfhydryl groups of the precursor cysteine compounds were alkylated by geranylgeranyl chloride. Geranylgeranyl chloride was prepared from N-chlorosuccinimide (Aldrich) and geranylgeraniol (Kuraray Co., Japan) as described (Davisson et al, Methods Enzymol. 110:130 (1985)). N-acetyl-S-farnesylcysteine methyl ester (AFCME) was prepared by acetylation of FCME (Bodansky et al, In: The Practice of Peptide Synthesis, New York: Springer-Verlag, p. 16–17 (1984)), except that 4-methylbenzyl chlorocarbonate was replaced by acetyl anhydride. The methylamides of FC and AFC (designated FCMA and AFCMA, respectively) were prepared by methylamine treatment of the corresponding methyl esters (ie FCME and AFCME) by standard procedures (Corson et al, Synth. 1:179 (1941)). The dipeptide γGlu-Cys was farnesylated as described for the cysteine compounds and subjected to COOH-methylation by a standard procedure involving treatment with diazomethane (Pizey, Synthetic Reagents, Ch. 2, John Wiley, New York (1974)). All compounds were purified by C18 reverse-phase HPLC chromatography prior to use.

Cell Culture

Sf9 cells were grown in Grace's insect culture media supplemented with 10% fetal bovine serum (HyClone), 0.1% Pluronic F-68, 100 unit/ml penicillin and 100 μg/ml streptomycin. Sf9 cells were infected with baculovirus according to established procedures (O'Reilly et al, Baculovirus Expression Vectors—A Laboratory Manual, New York: W.H. Freeman & Co. (1992)). Recombinant baculovirus containing the human MDR1V185 cDNA (Germann et al, Biochemistry 29:2295 (1990)) was provided by Dr. M. Gottesman (MDR1 cDNAs are available from the American Type Culture Collection, Rockville, Md.). Mock-infection was carried out using recombinant baculovirus containing the cDNA encoding a protein prenyltransferase. Conditions for maintaining the drug-sensitive human breast cancer cell line (MCF7WT) and its drug-resistant subline (MCF7-MDR) have been described (Blobe et al, J. Biol. Chem. 268:658 (1993)). These cells were grown in Iscove's Modified Dulbecco's Media (MDM) supplemented with 10% fetal bovine serum. The MCF7-MDR cells were exposed to 10 μM doxorubicin every 8–10 passages to maintain the drug-resistant phenotype.

Membrane Preparation

Sf9 membranes were prepared from cells harvested 3 days after infection with specified baculovirus as described (Sarkadi et al, J. Biol. Chem. 267:4854 (1992)). MCF7 membranes from both wild-type and drug-resistant cell lines were prepared by nitrogen cavitation procedures (Cornwell et al, J. Biol. Chem. 261:7921 (1986)), flash-frozen in liquid nitrogen, and stored at −80° C. until use.

ATPase Activity

P-gp-associated ATPase activity was measured by determining vanadate-sensitive release of inorganic phosphate from ATP as described (Sarkadi et al, J. Biol. Chem. 267:4854 (1992)). Sf9 membranes containing 5–10 μg protein were incubated in 100 μl of 50 mM Mes-Tris, pH 6.8, 50 mM KCl, 2 mM DTT, 2 mM EGTA, 1 mM ouabain, 5 mM sodium azide, 5 mM Mg/ATP. P-gp-associated ATPase activity in MCF7-MDR cells was measured using the same condition except that 50 mM Mes-Tris, pH 6.8 was replaced by 50 mM Tris-HCl, pH 7.5. Prenylcysteines and control drug (verapamil) were added in DMSO solutions with DMSO concentration in the reaction maintained at 1%. Reactions were conducted at 37° C. for 20 min.

[³H]-Azidopine Photoaffinity Labelling of
P-glycoprotein in Sf9 Membranes

Photoaffinity labelling of P-glycoprotein in Sf9 membranes was performed by modification of a previously described method (Safa et al, J. Biol. Chem. 262:7884 (1987)). Briefly, membranes (50≧60 μg protein/assay) were incubated in the presence of either prenylcysteine analogs, nicardipine, or vehicle (DMSO) for 30 minutes at 20° C. in 10 mM Tris-HCl, pH 7.5, 0.25 M sucrose. [³H]-azidopine (52 Ci/mmol, Amersham) was added to a final concentration of 0.5 μM and the samples were incubated an additional 20 minutes. The samples were photolabelled on ice by UV irradiation for 10 min. An equal volume (50 μl) of 2X Laemmli sample buffer was added and the samples were incubated an additional 5 minutes at 30° C., after which samples were processed on 7.5% polyacrylamide gels and photolabelled bands detected by fluorography.

Other Methods

Protein concentration was determined by a dye binding assay (Bio-Rad) using BSA as the standard (Bradford, Ana. Biochem. 72:248 (1976)). Immunoblot analysis was performed using the anti-P-gp monoclonal antibody C219 (Signet); visualization was performed by an alkaline phosphatase method according to manufacturer's instruction (Promega).

EXAMPLE 1

P-gp Expression

Figure 1A:
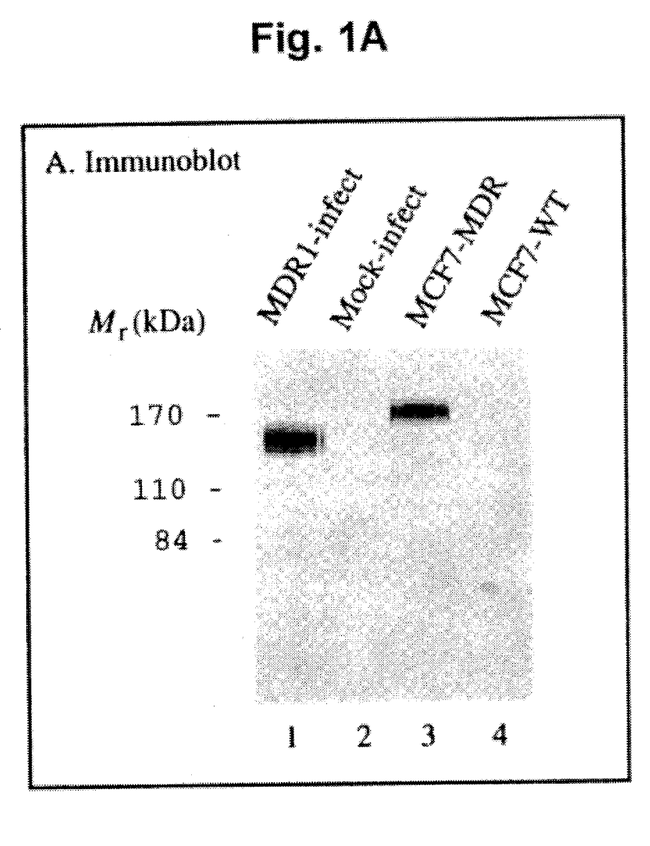
Figure 1B:
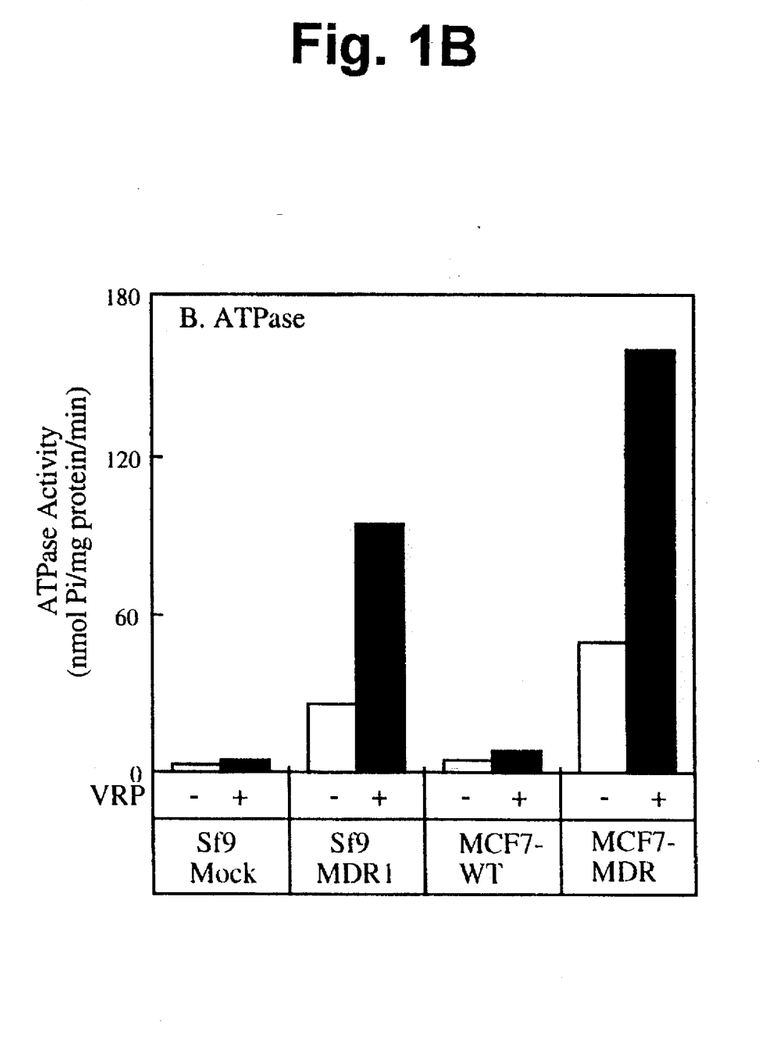

Expression of P-gp in Sf9 cells (via recombinant baculovirus infection) and human breast cancer MCF7 cells (through drug selection) is shown in FIG. 1. Sf9 cells produce a form of P-glycoprotein that migrates faster on SDS-PAGE than the transporter expressed in mammalian cells (FIG. 1A); this is due to an altered glycosylation of p-glycoprotein in Sf9 cells which does not affect its function (Germann et al, Biochemistry 29:2295 (1990)). Membranes isolated from the two cell types expressing P-gp displayed the characteristic vanadate-sensitive, drug (verapamil)-dependent ATP hydrolysis associated with this transporter (Sarkadi et al, J. Biol. Chem. 267:4854 (1992)), (Ambudkar et al, Proc. Natl. Acad. Sci. USA 89:8472 (1992)), while membranes from mock-infected Sf9 cells and from MCF7-WT cells did not have this activity (FIG. 1B).

EXAMPLE 2

Stimulation of P-gp ATPase Activity

Figure 2A:
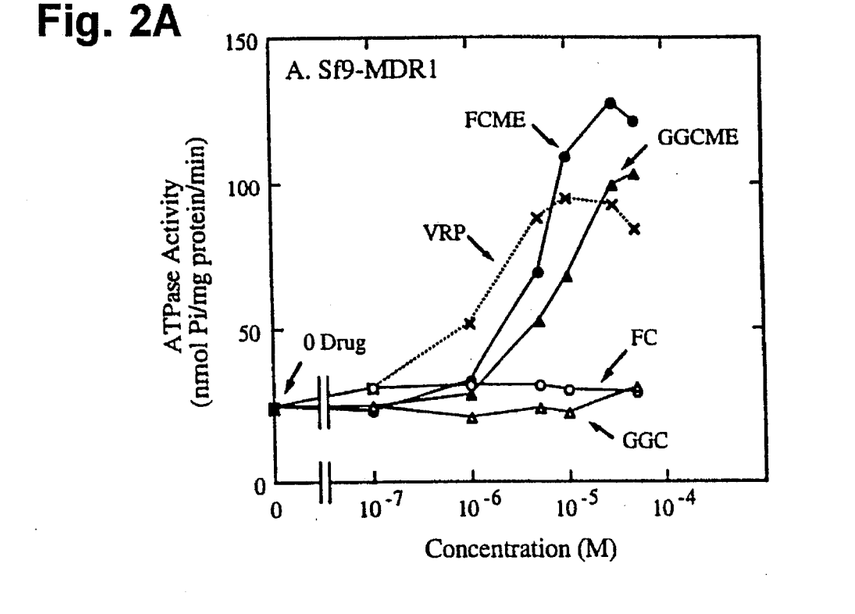

The first group of compounds prepared for testing on P-gp included farnesylcysteine (FC), geranylgeranylcysteine (GGC), and their respective methyl esters (FCME and GGCME); these compounds represent the C-terminal structures of prenylated proteins (Clarke, Ann. Rev. Biochem. 61:355 (1992)). While FC and GGC were ineffective in stimulating the ATPase of P-gp expressed in Sf9 cells, both FCME and GGCME stimulated this activity in a fashion very similar to that of verapamil (FIG. 2A). The maximum stimulation by the two methylated prenylcysteines was 4–5 fold at concentrations of 10–20 μM. These results indicate that these prenylcysteines can functionally interact with P-gp and that methylation of the α-carboxyl group is an important determinant in this interaction.

Figure 2B:
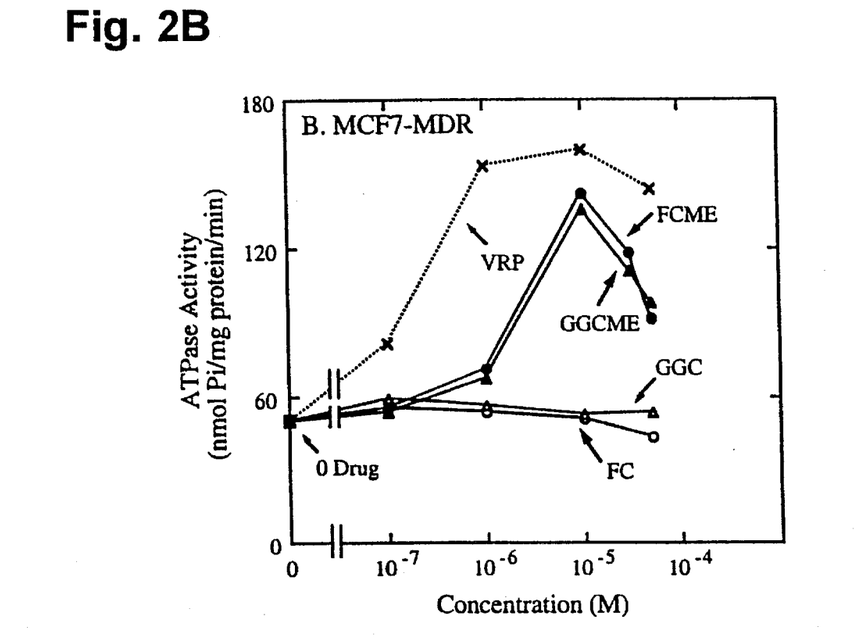

To confirm that the interaction of the prenylcysteines with P-gp was not simply a product of expression of this transporter in Sf9 cells, these compounds were also tested on the native P-gp expressed in the drug-resistant human breast cancer cell line MCF7-MDR. In membranes isolated from this cell line, P-gp-catalyzed ATP hydrolysis was increased ~2.5-fold by FCME and GGCME (FIG. 2B). The dose-dependence of the stimulation was similar to that seen in the Sf9 membranes, although the verapamil effect was observed at somewhat lower concentrations. Again, neither of the unmethylated prenylcysteines showed activity.

EXAMPLE 3

Figure 3:
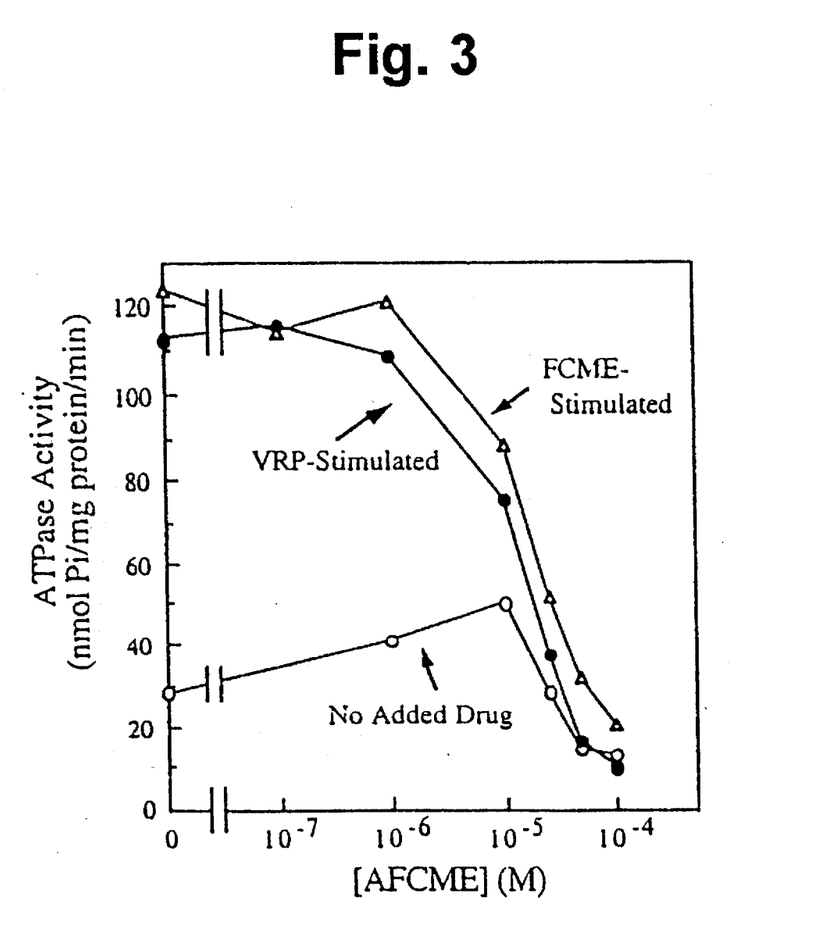
FIG. 3. Ability of acetyl farnesyl methylester (AFCME) to block drug stimulated ATPase of MDR. The effect of AFCME on the basal ATPase activity of MDR(○) and that stimulated by FCME (△) and verapamil (●) is shown.

Competitive Inhibition of Drug-Stimulated ATPase of MDR by Acetyl Farnesyl Methyl Ester Preliminary analysis of the effect of AFCME on P-gp ATPase activity revealed a weak stimulation of the ATPase activity at low (<20 μM) concentrations, but a marked inhibition of even the basal ATPase activity at higher concentrations. These results indicated that AFCME could be an inhibitor or antagonist of P-gp. To examine this in greater detail, the effect of AFCME on both basal and drug (FCME, verapimil)-stimulated ATPase activity of P-gp was assessed. The results are shown in FIG. 3 and reveal that AFCME can block both the basal and drug-stimulated ATPase activities of P-gp in a dose-dependent fashion. These results indicate that AFCME acts as a P-gp antagonist.

EXAMPLE 4

Figure 4A:
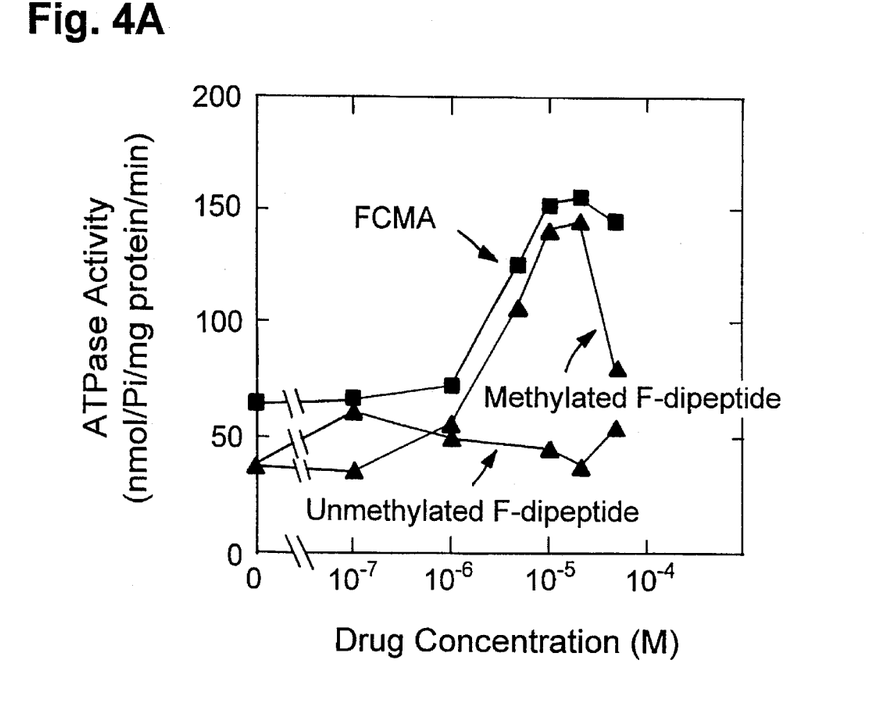
Figure 4B:
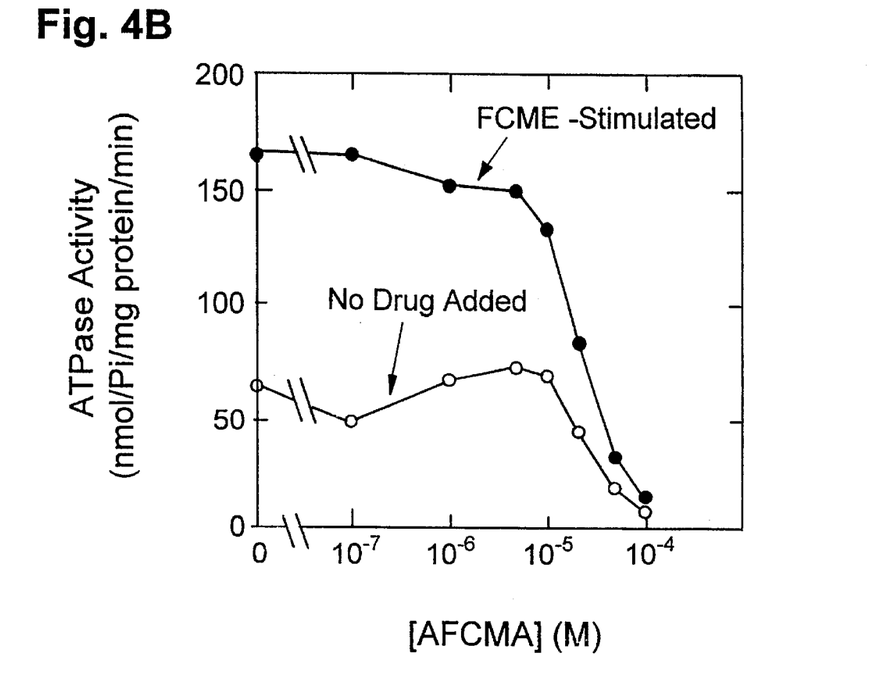

Interaction of Prenylcysteine Methylamides and Prenylcysteine-Containing Dipeptides with P-gp The C-methylamides of FC and AFC (designated FCMA and AFCMA, respectively) are also potent in stimulation (FCMA) and inhibition of drug-stimulated (AFCMA) P-gp ATPase activities (FIG. 4) in a fashion essentially indistinguishable from their C-methylated counterparts (FIGS. 2 and 3). These results indicate that substitutions of the C-methyl group of the prenylcysteine methyl esters can be tolerated with retention of P-gp-modulating activity. Furthermore, the methylamide-containing compounds have the advantage of greater chemical stability. Compounds containing a carbon atom instead of an oxygen or nitrogen bridging the methyl and the α-carbon of the cysteine residue can be expected to be advantageously stable as well.

The ability of the farnesylated dipeptide of γGlu-Cys to stimulate P-gp ATPase activity in a methylation-dependent fashion (FIG. 4) indicates the potential to place substituents on the α-NH₂ group of the prenylcysteine while retaining P-gp modulating activity. Thus, the invention includes N-substituted prenylcysteines.

EXAMPLE 5

Specificity of Interaction of Prenylcyteine Methyl Esters and P-gp

Figure 5:
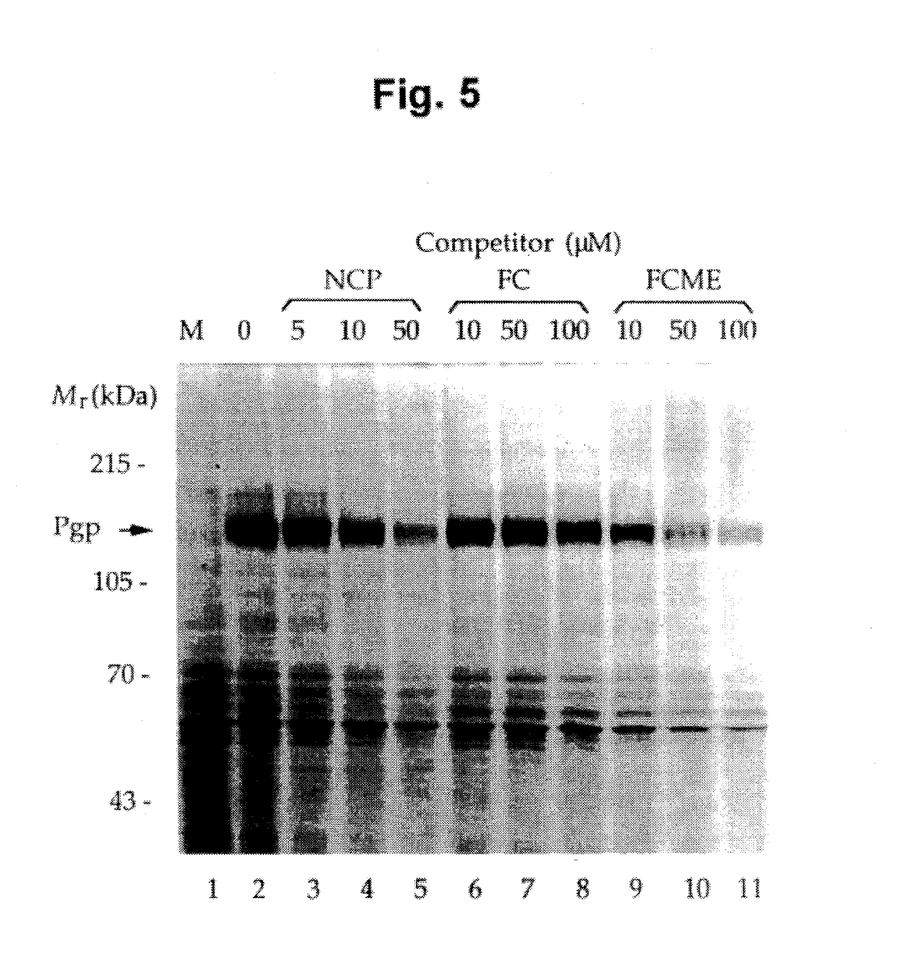

Further evidence that prenylcysteine methyl esters were interacting specifically with P-gp was obtained by examining inhibition of photoaffinity labelling of the transporter by [³H]-azidopine, a photo-activatable substrate of P-glycoprotein (Safa et al, J. Biol. Chem. 262:7884 (1987)) the binding of which is competed for by drugs that are substrates for the transporter (Gottesman et al, Ann. Rev. Biochem. 62:385 (1993)), (Safa et al, J. Biol. Chem. 262:7884 (1987)). Membranes isolated from Sf9 cells expressing P-gp and subject to [$^3$H]-azidopine labelling demonstrated that the major radiolabelled component was the transporter; no such labelling was seen in membranes from mock-infected Sf9 cells (FIG. 5, lanes 5 and 2). Addition of FCME to the labeling reaction markedly diminished the labeling of the transporter (FIG. 5, lanes 9–11) similar to that seen with the control drug nicardipine (FIG. 5, lanes 3–5), while unmethylated FC had little effect (FIG. 5, lanes 6–8).

EXAMPLE 6

Characterization of Structural Features Involved in Interaction of Methylated Prenylcysteine with P-gp To further characterize the structural features involved in the interaction of methylated prenylcysteines with P-gp, a group of related compounds was examined using the ATPase-stimulation assay; these results are summarized in Table 1. Cysteine methyl ester itself was not active even at 400 μM, suggesting a critical role for the isoprenoid. In addition, the free isoprenoid farnesol was ineffective. AFC, produced by acetylation of the amino group of FC, did not stimulate the transporter's ATPase activity, providing further evidence that the stimulation observed with FCME reflects specific recognition of this ligand rather than simply a hydrophobic effect as a consequence of methylation of FC. Acetylation of the amino group of FCME, producing AFCME, essentially abolished its stimulatory effect; instead AFCME inhibited the transporter's basal ATPase activity at concentration >20 μM.

TABLE 1

Stimulation of P-glycoprotein ATPase activity by prenylcysteine compounds
ATPase activity in membranes from Sf9 cells expressing MDR1 was measured in the presence of the indicated compounds at concentrations to 50 μM.

| Compound | Structure | Stimulation of ATPase Activity |
|---|---|---|
| FCME | \-Farnesyl-SCH$_2$CHCOOCH$_3$\-<br>\|<br>NH$_3$$^+$ | +++$^a$ |
| GGCME | \-Geranylgeranyl-SCH$_2$CHCOOCH$_3$\-<br>\|<br>NH$_3$$^+$ | +++ |
| FC | \-Farnesyl-SCH$_2$CHCOO$^-$\-<br>\|<br>NH$_3$$^+$ | − |
| GGC | \-Geranylgeranyl-SCH$_2$CHCOO$^-$\-<br>\|<br>NH$_3$$^+$ | − |
| AFC | \-Farnesyl-SCH$_2$CHCOO$^-$\-<br>\|<br>CH$_3$CONH | − |
| AFCME | \-Farnesyl-SCH$_2$CHCOOCH$_3$\-<br>\|<br>CH$_3$CONH | ±$^b$ |
| F—OH | Farnesol | − |
| CME | \-HSCH$_2$CHCOOCH$_3$\-<br>\|<br>NH$_3$$^+$ | − |
| FCMA | \-Farnesyl-SCH$_2$CHCONHCH$_3$\-<br>\|<br>NH$_3$$^+$ | +++ |
| AFCMA | \-Farnesyl-SCH$_2$CHCONHCH$_3$\-<br>\|<br>CH$_3$CONH | ± |
| F-γGlu-Cys | \-Farnesyl-SH$_2$CHCOO$^-$\-<br>\|<br>NHCOCH$_2$CH$_2$CHCOO$^-$<br>\|<br>NH$_3$$^+$ | − |
| F-γGlu-Cys Methyl Ester | \-Farnesyl-SCH$_2$CHCOOCH$_3$\-<br>\|<br>NHCOCH$_2$CH$_2$CHCOOCH$_3$<br>\|<br>NH$_3$$^+$ | +++ |

$^a$Maximal stimulation was ~4.5 fold. $^b$In the presence of 5–10 μM AFCME or AFCMA, ATPase activity was increased ~2-fold; at higher concentrations, this compound exhibited inhibitory effect.

All documents cited above are hereby incorporated in their entirety by reference.

One skilled in the art will appreciate from a reading of this disclosure that various changes in form and detail can be made without departing from the true scope of the invention. One skilled in the art will appreciate, for example, that the prenylcysteines, and analogs thereof, described herein have diagnostic potential due to their affinity for membrane transporters.

What is claimed is:

1. A method of inhibiting or reversing the resistance of cells to the effects of a drug with which said cells are treated comprising contacting said cells with a compound, or pharmaceutically acceptable salt thereof, of the formula (I):

wherein:

R$^1$ is a straight or branched chain alkyl, alkene or alkyne of 10–20 carbon atoms;

R$^2$ is —CH$_3$, —NH$_2$, —OX, —NHX, NX$_2$, —CH$_2$X, —(CH$_2$)$_n$CH(X)$_2$ or —(CH$_2$)$_n$C(X)$_3$, wherein n is 1–5 and X is an alkyl of 1–4 carbon atoms and ;

NR$^3$ is , —N(Y)$_3$$^+$ wherein Y is hydrogen or an alkyl of 1–4 carbon atoms, —NHCOZ wherein Z is an alkyl of 1–4 carbon atoms, or an amino acid residue, in an amount sufficient to effect expression in said cells of a membrane transporter of said drug and thereby effect said inhibition or reversal.

2. The method according to claim 1 wherein R$^1$ includes an isoprene unit.

3. The method according to claim 2 wherein $R^1$ includes 2 to 5 isoprene units.

4. The method according to claim 1 wherein $R^2$ is OX and X is methyl.

5. The method according to claim 1 wherein $R^2$ is —NHX and X is methyl.

6. The method according to claim 1 wherein $NR^3$ is —$NH_{3+}$.

7. The method according to claim 1 wherein $R^3$ is —NHCOZ and Z is ethyl.

8. The method according to claim 1 wherein said cells are mammalian cells.

9. The method according to claim 1 wherein said cells are cancer cells.

10. The method according to claim 1 wherein said transporter is a product of the MDR1, MDR2, MRP or pfmdr gene.

11. The method according to claim 10 wherein said transporter is P-glycoprotein.

12. S-prenylcysteine C-alkylamide of the formula:

wherein:

$R^1$ is prenyl;

$R^2$ is an alkylamide; and

$R^3$ is hydrogen.

13. A composition comprising the compound according to claim 12 and a pharmaceutically acceptable carrier.

14. The S-prenylcysteine C-alkylamide according to claim 12 wherein C-alkylamide is a C—$(C_1-C_4)$alkylamide.

15. The composition according to claim 13 wherein said compound is S-prenylcysteine C—$(C_1-C_4)$alkylamide.

16. A method of assaying a test compound for the ability to competitively inhibit a P-glycoprotein (P-gp)-associated activity comprising reacting said test compound with P-glycoprotein in the presence of a compound of formula (I):

wherein:

$R^1$ is a straight or branched chain alkyl, alkene or alkyne of 10–20 carbon atoms;

$R^2$ is —$CH_3$, —$NH_2$, —OX, —NHX, $NX_2$, —$CH_2X$, —$(CH_2)_nCH(X)_2$ or —$(CH_2)_nC(X)_3$, wherein n is 1–5 and X is an alkyl of 1–4 carbon atoms and;

$NR^3$ is—$N(Y)_3^+$ wherein Y is hydrogen or an alkyl of 1–4 carbon atoms, —NHCOZ wherein Z is an alkyl of 1–4 carbon atoms, or an amino acid residue, and comparing the resulting P-gp-associated activity with that of a control sample, an inhibition in P-gp-associated activity being indicative of a competitive inhibitor.

17. A method of blocking a membrane transporter of a cell comprising contacting said cell with a compound, or pharmaceutically acceptable salt thereof, of the formula (I):

wherein:

$R^1$ is a straight or branched chain alkyl, alkene or alkyne of 10–20 carbon atoms;

$R^2$ is —$CH_3$, —$NH_2$, —OX, —NHX, $NX_2$, —$CH_2X$, —$(CH_2)_nCH(X)_2$ or —$(CH_2)_nC(X)_3$, wherein n is 1–5 and X is an alkyl of 1–4 carbon atoms and;

$NR^3$ is—$N(Y)_3^+$ wherein Y is hydrogen or an alkyl of 1–4 carbon atoms, —NHCOZ wherein Z is an alkyl of 1–4 carbon atoms, or an amino acid residue, in an amount sufficient to effect said blocking.

* * * * *